United States Patent
Yoon et al.

(10) Patent No.: US 9,855,119 B2
(45) Date of Patent: Jan. 2, 2018

(54) DENTAL IMPLANT FIXTURE

(75) Inventors: Ji Hoon Yoon, Busan (KR); Sang Oh Park, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 0 days.

(21) Appl. No.: 13/384,810

(22) PCT Filed: Jul. 27, 2010

(86) PCT No.: PCT/KR2010/004902
§ 371 (c)(1),
(2), (4) Date: Jan. 19, 2012

(87) PCT Pub. No.: WO2011/013973
PCT Pub. Date: Feb. 3, 2011

(65) Prior Publication Data
US 2012/0156647 A1    Jun. 21, 2012

(30) Foreign Application Priority Data
Jul. 27, 2009   (KR) .................. 20-2009-0009820 U

(51) Int. Cl.
*A61C 8/00*    (2006.01)

(52) U.S. Cl.
CPC ............ *A61C 8/005* (2013.01); *A61C 8/0025* (2013.01); *A61C 8/0024* (2013.01)

(58) Field of Classification Search
CPC ....... A61C 8/00; A61C 8/0021; A61C 8/0022; A61C 8/0024; A61C 8/0025
USPC .............. 433/172–176, 201.1; 606/301–331; 411/411
See application file for complete search history.

(56) References Cited

U.S. PATENT DOCUMENTS

| | | | |
|---|---|---|---|
| 5,000,686 A * | 3/1991 | Lazzara et al. | 433/174 |
| 5,199,873 A * | 4/1993 | Schulte et al. | 433/174 |
| 5,642,996 A * | 7/1997 | Mochida et al. | 433/174 |
| 6,340,300 B1 * | 1/2002 | Padros Fradera | 433/174 |
| 2004/0146834 A1 | 7/2004 | Haessler | |
| 2007/0287128 A1 | 12/2007 | Claudio et al. | |
| 2008/0014556 A1 * | 1/2008 | Neumeyer | 433/174 |
| 2008/0215099 A1 * | 9/2008 | Balfour et al. | 606/306 |

(Continued)

FOREIGN PATENT DOCUMENTS

| CN | 1033558 A | 7/1989 |
|---|---|---|
| CN | 1984618 A | 6/2007 |

(Continued)

OTHER PUBLICATIONS

International Search Report: dated Apr. 22, 2014; PCT/KR2010/004902.

(Continued)

*Primary Examiner* — Yogesh Patel
(74) *Attorney, Agent, or Firm* — Ladas & Parry LLP

(57) ABSTRACT

An implant fixture that is inserted into a bone tissue formed of a cortical bone and a cancellous bone while rotating on a central axis to thereby form an artificial tooth root, the implant fixture including a first portion that is inserted into the cortical bone and includes a first screw thread having first peaks and first roots alternating with one another on an outer surface of the first portion; and a second portion that is disposed below the first portion and inserted into the cancellous bone.

6 Claims, 5 Drawing Sheets

(56) References Cited

U.S. PATENT DOCUMENTS

| | | | | |
|---|---|---|---|---|
| 2010/0055644 A1* | 3/2010 | Arni | ................ | A61C 8/0022 |
| | | | | 433/174 |
| 2010/0055645 A1* | 3/2010 | Mullaly et al. | ............... | 433/174 |
| 2011/0117522 A1* | 5/2011 | Verma et al. | ................ | 433/174 |

FOREIGN PATENT DOCUMENTS

| | | | |
|---|---|---|---|
| CN | 101297772 A | 11/2008 | |
| CN | 101366664 A | 2/2009 | |
| JP | 2003-038522 A | 2/2003 | |
| JP | 1020090077982 A | 7/2009 | |
| KR | 1020090057911 A | 6/2009 | |
| KR | 1020090065077 A | 6/2009 | |
| KR | 2030090076077 A | 6/2009 | |
| WO | 2005/117742 A1 | 12/2005 | |
| WO | 2007086622 A1 | 8/2007 | |

OTHER PUBLICATIONS

First Chinese Office Action dated Dec. 16, 2013; Appln. No. 201080031879.6.

Third Chinese Office Action dated Dec. 15, 2014; Appln. No. 201080031879.6.

Second Chinese Office Action dated Jul. 15, 2014; Appln. No. 201080031879.6.

* cited by examiner

DENTAL IMPLANT FIXTURE

TECHNICAL FIELD

The present invention relates to a dental implant fixture, and more particularly, to a dental implant fixture that can be certainly implanted into a bone tissue while a sharp increase of implantation torque is reduced, when the dental implant fixture is inserted into a cortical bone.

BACKGROUND ART

A screw type implant fixture includes a body having a screw thread formed on an outer surface thereof and is used as a fixing unit to fix a dental or orthopedic prosthesis or the like into a bone. A bone tissue into which a fixture is to be inserted consists of cancellous and cortical bones. A cancellous bone refers to a relatively soft bone tissue of a bone, and a cortical bone refers to a relatively thin film that is harder than a cancellous bone and generally encloses a cancellous bone. A length of a cancellous bone is usually longer than that of a cortical bone and thus an inserted fixture is implanted into a cancellous bone.

FIG. 1 is a diagram of an implant fixture 100 according to the related art. The implant fixture 100 is formed of a body portion 110 in which a plurality of screw threads 111 are vertically formed, and an entry portion 120 arranged below the body portion 110 and having a cut groove 121 that is formed. The implant fixture 100 according to the related art has a problem in that a torque generated due to inserting of the implant fixture 100 by using repetitive rotation is relatively great at the beginning but is gradually decreased, which reduces an initial fixing force. When the initial fixing force is low, the implant fixture 100 is not certainly implanted in a bone tissue and thus, if an external force is applied to the implant fixture 100, an initial position may be changed or damage may be applied to a peripheral bone tissue.

FIG. 2 is a diagram of an implant fixture 200 according to the related art. The implant fixture 200 according to the related art is formed of a body portion 210 in which a plurality of screw threads are formed, and an entry portion 220 arranged below the body portion 210 and having a cut groove 221 that is formed in the entry portion 220. Here, the body portion 210 is formed of a first part 211 in which a plurality of fine screw threads 211a are formed at an upper part of the body portion 210, and a second part 212 in which a plurality of macro screw threads 212a are formed at a lower part of the body portion 210.

The implant fixture 200 according to the related art is advantageous in that a initial fixing force is relatively great during an insertion procedure due to that the number of the fine screw threads 211a of the first part 211 is increased compared to the number of the macro screw threads 212a of the second part 212, and thus the implant fixture 200 can be firmly implanted into a bone tissue.

DISCLOSURE OF INVENTION

Technical Problem

However, since the number of screw threads in the implant fixture 200 is sharply increased while an implanting operation is performed from the second part 212 to the first part 211, there is a possibility that an implantation torque is significantly increased between the second part 212 and the first part 211. That is, since the number of fine screw threads 211a of the first part 211 is increased compared to the number of the macro screw threads 212a of the second part 212, a new screw groove is formed on an external wall of a peripheral bone tissue where the implanting operation is performed, and thus the implantation torque can be significantly increased while forming the new screw groove. The significant increase of the implantation torque may cause bone absorption. The bone absorption indicates a phenomenon in which a portion of the bone tissue where the implant fixture 200 is implanted is reduced and then atrophied. The bone absorption weakens the fixing force of the implant fixture 200 such that stability of the implant fixture 200 may be degraded, or a prosthesis attached on the implant fixture 200 may be damaged.

Solution to Problem

The present invention provides a dental implant fixture capable of sufficiently increasing an initial fixing force while an implantation torque is not significantly increased.

According to an aspect of the present invention, there is provided an implant fixture that is inserted into a bone tissue formed of a cortical bone and a cancellous bone while rotating on a central axis to thereby form an artificial tooth root, the implant fixture including a first portion that is inserted into the cortical bone and includes a first screw thread having first peaks and first roots alternating with one another on an outer surface of the first portion; and a second portion that is disposed below the first portion and inserted into the cancellous bone, wherein a second screw thread having second peaks and second roots alternating with one another is formed on an outer surface of the second portion, wherein distances between adjacent second peaks of the second screw thread are equal to distances between adjacent first peaks of the first screw thread, and wherein outer diameters of the second screw thread are the same in up and down directions and inner diameters of the second screw thread are less than inner diameters of the first screw thread; and a third portion that is disposed below the second portion and inserted into the cancellous bone, wherein a third screw thread having third peaks and third roots alternating with one another on an outer surface of the third portion, and wherein a cutting edge caved to be more adjacent to the central axis than the third roots is arranged in the third portion, wherein the first screw thread and the second screw thread have at least double threads.

All of the first peaks of the first screw thread and the second peaks of the second screw thread may be lied on a same plane.

The inner diameters of the second screw thread may be less than the inner diameters of the first screw thread by 0.1 to 1.0 mm.

When the distances between adjacent first peaks of the first screw thread are referred to as S1 and the distances between adjacent second peaks of the second screw thread are referred to as S2, S1 and S2 may be between 0.6 to 1.0 mm.

The distances that the first screw thread and the second screw thread move per one rotation along a central axis may be the same, and the distances may be between 0.5 to 2.5 mm.

Advantageous Effects of Invention

A dental implant fixture according to the present invention has a structure in which inner diameters of second screw threads are less than inner diameters of first screw threads so that implantation torque is gradually increased while an implanting operation is performed from a second portion to a first portion. Accordingly, it is possible to sufficiently increase an initial fixing force.

In addition, since distances between adjacent second peaks of the second screw thread are equal to distances between adjacent first peaks of the first screw thread, torque is not sharply increased and thus implantation may be stably performed without a risk of bone absorption.

Also, since the first and second screw threads have more than double threads, an implanting time period may be reduced, compared to that of a screw thread having single thread, and stress applied to a peripheral bone tissue is low and thus a stress dispersion effect is great.

BRIEF DESCRIPTION OF DRAWINGS

The above and other features and advantages of the present invention will become more apparent by describing in detail exemplary embodiments thereof with reference to the attached drawings in which.

BEST MODE FOR CARRYING OUT THE INVENTION

Exemplary embodiments of the present invention will now be described in detail with reference to the attached drawings.

Figure 8:
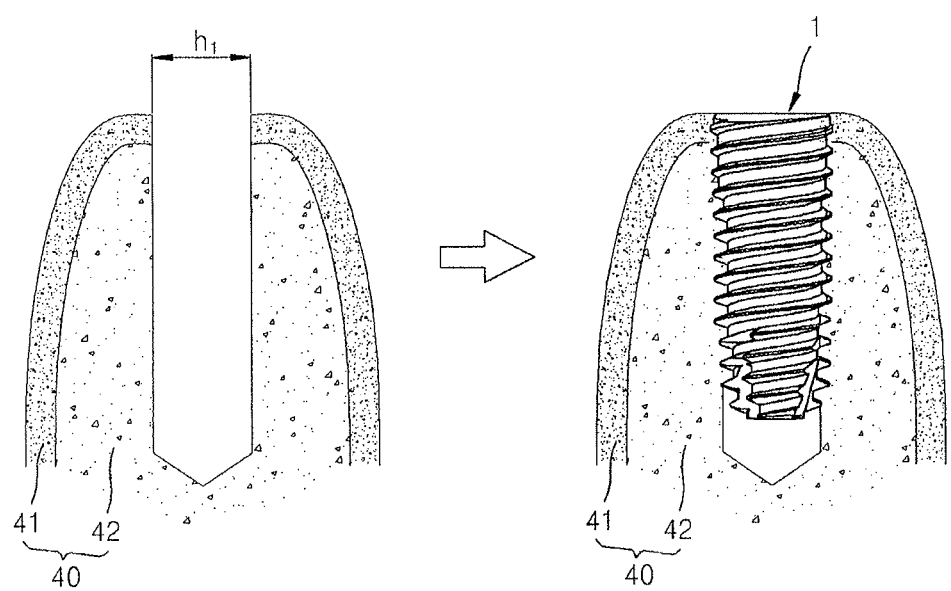
FIG. 8 is a diagram for illustrating insertion of the implant fixture of FIG. 3 into a bone tissue of a human body.

An implant fixture 1 for a dental purpose according to an embodiment of the present invention may be inserted into a bone tissue 40 consisting of a cortical bone 41 and a cancellous bone 42 so as to form an artificial tooth root refer to FIG. 8. The implant fixture 1 has a cylindrical shape and an outer surface on which a screw thread is formed. When the implant fixture 1 rotates along a central axis C (refer to FIG. 3), the implant fixture 1 is inserted into the cortical bone 41 and the cancellous bone 42 to form screw roots at an inner surface of an implant hole formed in the bone tissue 40 using a drill in advance. Here, the implant fixture 1 may be formed of titanium or any metal material that is not rejected by the human body.

The implant fixture 1 is formed of a first portion 10, a second portion 20, and a third portion 30. The first portion 10 refers to a portion of the implant fixture 1 that is mostly inserted into the cortical bone 41 when the implant fixture 1 is inserted (the portion of the first portion 10 may also be implanted into the cancellous bone 42). The first portion 10 forms an upper part of the implant fixture 1. A first screw thread 11 is formed on an outer surface of the first portion 10. The first screw thread 11 has a spiral form, and includes first peaks 11a and first roots 11b alternating with one another along the central axis C.

The second portion 20 is disposed below the first portion 10. The second portion 20 is integrally coupled to the first portion 10, but the form of the second portion 20 is not limited thereto, and for example, a screw thread structure may be disposed between the first portion 10 and the second portion 20.

The second portion 20 refers to a portion of the implant fixture 1 that is mostly inserted into the cancellous bone 42 when the implant fixture 1 is inserted (the portion of the second portion 20 may also be implanted into the cortical bone 41). The second portion 20 forms a lower part of the implant fixture 1.

A second screw thread 21 is formed on an outer surface of the second portion 20. The second screw thread 21 has a spiral form, and includes second peaks 21a and second roots 21b alternating with one another along the central axis C.

Distances (a pitch S2) between adjacent second peaks 21a of the second screw thread 21 are equal to distances (a pitch S1) between adjacent first peaks 11a of the first screw thread 11 (that is, S2=S1). In this manner, since the distances between the first and second peaks 11a and 21a of the first and second screw threads 11 and 21 are the same, an implantation torque may not be significantly increased. That is, while the first portion 10 is implanted after the second portion 20 is implanted, neither the distances between the peaks of the first and second screw threads 11 and 21 become narrow nor a new female screw thread is formed in an inner wall of a bone tissue, and thus the implantation torque may not be significantly increased and thus a peripheral bone tissue may not be damaged.

Meanwhile, outer diameters D2 of the second screw thread 21 are the same in up and down directions. That is, the outer diameters D2 of the second screw thread 21, which are formed by the second peaks 21a, are constantly maintained from an upper part of the second portion 20 toward a lower part of the second portion 20. Accordingly, while the second portion 20 is implanted, neither an excessive pressure is applied to a peripheral bone tissue nor a torque is decreased.

Also, distances that the first screw thread 11 and the second screw thread 21 move per one rotation along a central axis are the same. If the distances that the first screw thread 11 and the second screw thread 21 move per one rotation along the central axis are different, a greater rotational torque is required during implantation, and this may apply a strong pressure on a peripheral bone tissue and cause cracks therein. Here, a movement distance that the implant fixture 1 moves per one rotation may be between 0.5 to 2.5 mm.

In addition, inner diameters d2 (also referred to as bone diameters) of the second screw thread 21 may be less than inner diameters d1 of the first screw thread 11. In more detail, the inner diameters d2 may be less than the inner diameters d1 by a difference of about 0.1 to 1.0 mm. When the inner diameters d2 of the second screw thread 21 are set to be less than the inner diameters d1 of the first screw thread 11, a sufficient pressure is applied to a peripheral bone tissue while implantation is performed from the second portion 20 to the first portion 10, and thus it is possible to gain a sufficient initial fixing force.

Also, the first peaks 11a of the first screw thread 11 and the second peaks 21a of the second screw thread 21 lie on a same plane. That is, outer diameters D1 of the first screw thread 11 and the outer diameters D2 of the second screw thread 21 may be the same. Accordingly, while the first portion 10 is implanted after the second portion 20 is implanted, the implantation torque is neither sharply decreased nor sharply increased, and thus the implantation may be easily performed.

The first screw thread 11 and the second screw thread 21 may have multiple threads. That is, more than double threads may be formed in the first screw thread 11 and the second screw thread 21. Also, the number of threads of the first screw thread 11 per one lead ('lead' indicates the distance that a peak of a screw thread moves when the implant fixture 1 rotates one round along a central axis C) may be equal to the number of threads of the second screw thread 21 per one lead.

Figure 3:
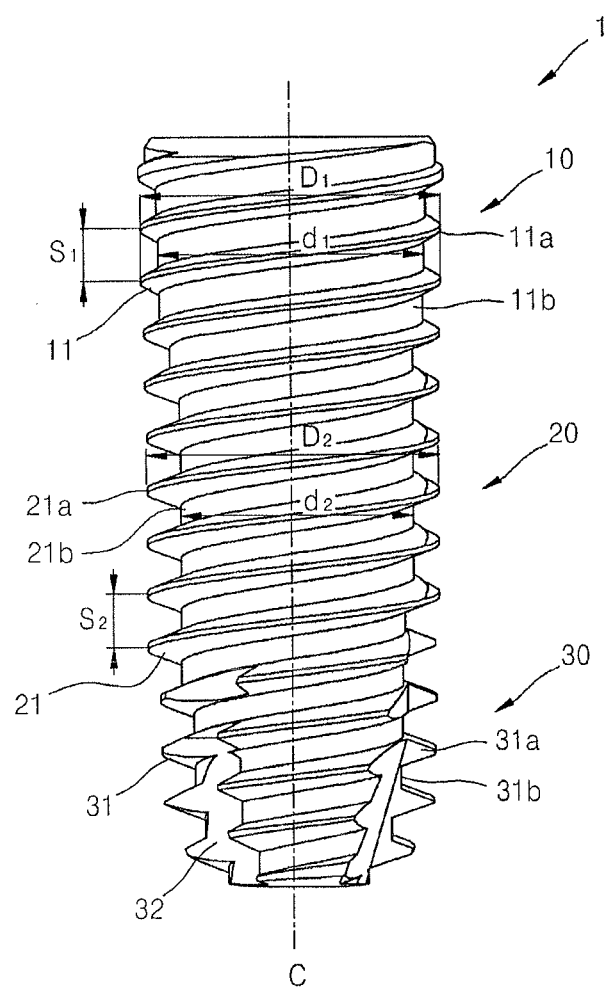
FIG. 3 is a diagram of an implant fixture according to an embodiment of the present invention.

The first screw thread 11 and the second screw thread 21 may be continuously connected to each other. In more detail, as illustrated in FIG. 3, the second screw thread 21 is continuously connected to the first screw thread 11, and the first screw thread 11 is continuously connected to another second screw thread 21. Since the first screw thread 11 and the second screw thread 21 are continuously connected to each other, the implant fixture 1 may be naturally implanted without a sharp increase of the implantation torque.

The third portion 30 is disposed below the second portion 20, and has a third screw thread 31 having third peaks 31a and third roots 31b alternating with one another on an outer surface of the third portion 30, and has a cutting edge 32 caved to be more adjacent to the central axis C than the third roots 31b. The third portion 30 forms a lowest part of the implant fixture 1, and indicates a part of the implant fixture 1 to be initially inserted into a bone tissue. That is, the third portion 30 indicates a part that is initially inserted into a bone tissue and forms a female screw thread in the bone tissue. The third portion 30 has the deeply caved cutting edge 32, and thus may be easily inserted into a bone tissue.

Figure 1:
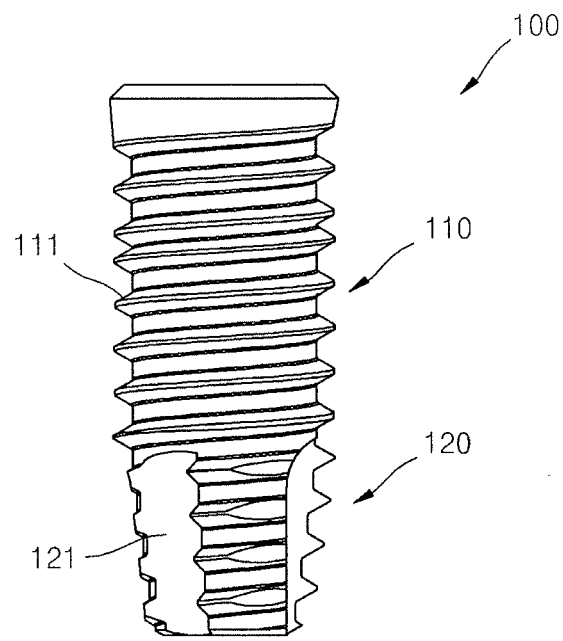
FIG. 1 is a diagram of an implant fixture according to the related art.
Figure 2:
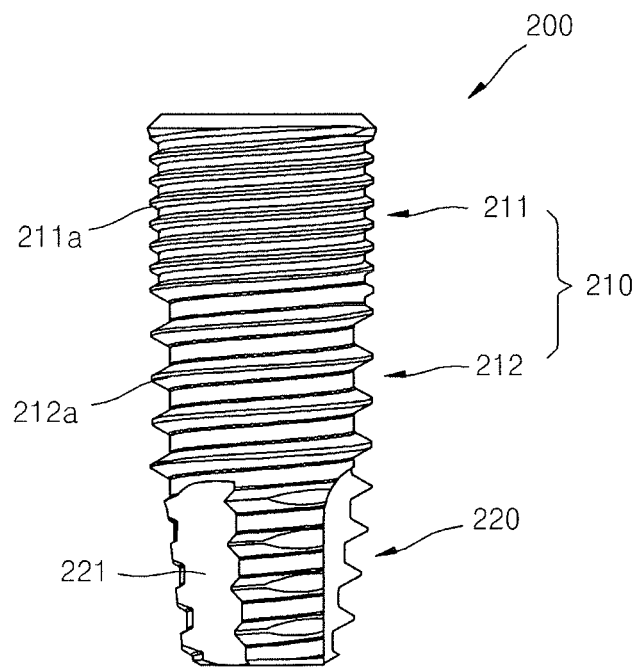
FIG. 2 is a diagram of another implant fixture according to the related art.
Figure 4:
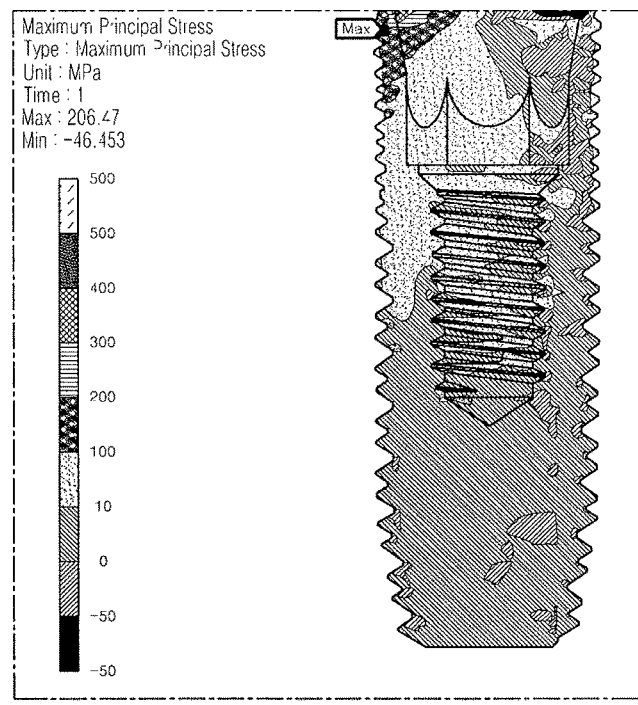
FIGS. 4 through 7 are diagrams for comparing equivalent stresses of implant fixtures according to the related art with an equivalent stress of the implant fixture according to the embodiment of the present invention.
Figure 5:
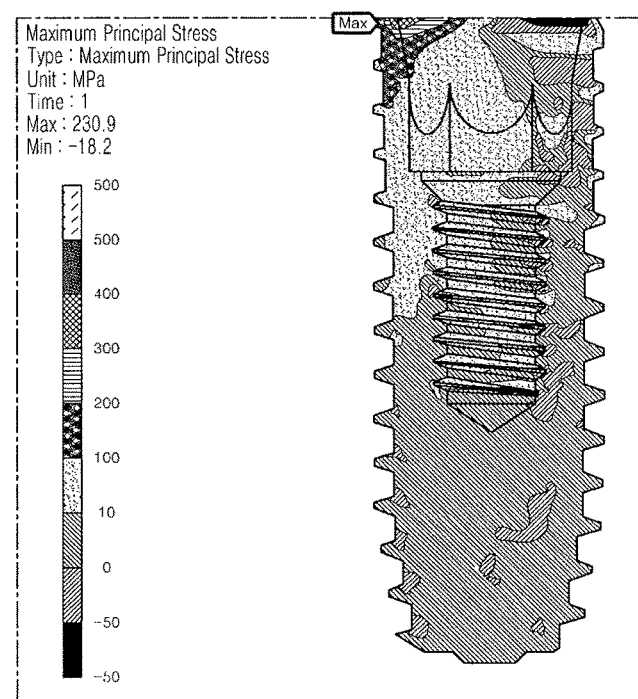
Figure 6:
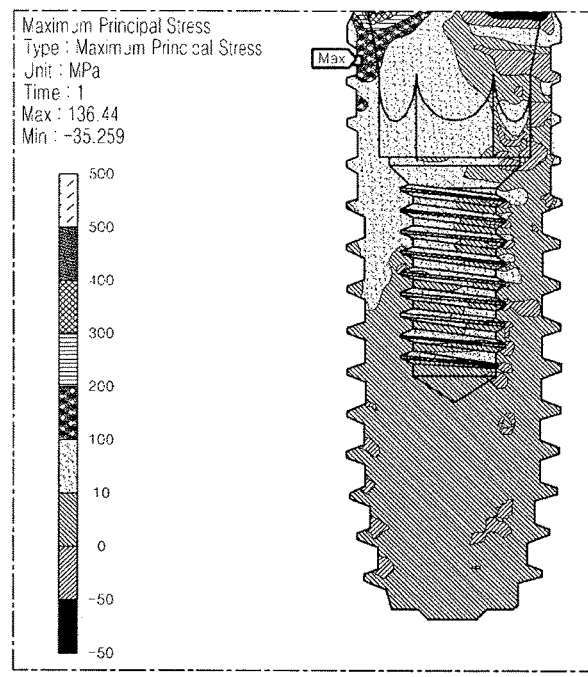

Meanwhile, with respect to the implant fixture 1 according to the present embodiment, a Finite Element Analysis (FEA) has been performed. In the FEA, maximum equivalent stresses are calculated by using an implant in FIG. 4 (having a structure similar to that of an implant fixture 200 of FIG. 2), an implant in FIG. 5 (having a structure similar to that of the implant fixture 1 of FIG. 3 having only one thread), and an implant in FIG. 6 (having the same structure as the implant fixture 1 of FIG. 3 having two threads).

Figure 7:
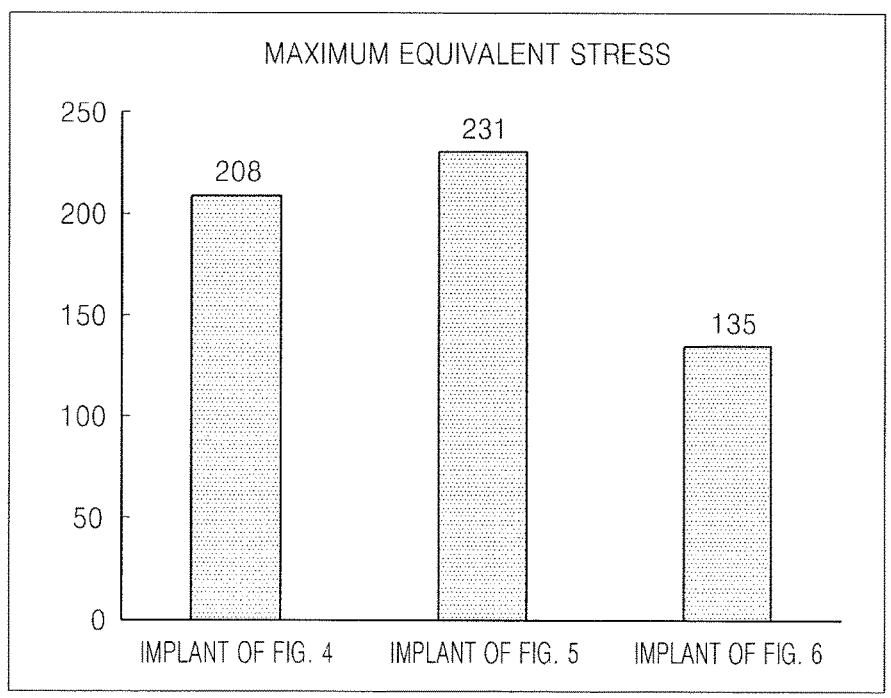

That is, in the FEA, the maximum equivalent stresses affecting respective peripheral bones when the implants are implanted to peripheral bone structures, respectively, are calculated. As illustrated in FIG. 7, according to a result of the calculation, it is possible to see that the maximum equivalent stress of the present embodiment (the implant in FIG. 6) is lower than those of other implants and thus a stress dispersion effect of the present embodiment is great.

The implant fixture 1 according to the present embodiment has operational effects as stated below. First, as illustrated in a left portion of FIG. 8, an implant hole having a diameter h1 is formed in a bone tissue with a drill and the implant fixture 1 is inserted into the implant hole. In more detail, the implant fixture 1 is inserted while rotating around a central axis. Here, a cutting edge at a lowest part of the implant fixture 1 forms a female screw thread groove in a peripheral bone tissue, and simultaneously, a third portion is inserted into the bone tissue. After the cutting edge is inserted into the bone tissue, a second portion is completely inserted so that a female screw thread is formed on an external wall of the bone tissue. After the insertion of the second portion is complete, a first portion is inserted into the bone tissue. In this regard, the completed insertion of the implant fixture 1 is illustrated in a right portion of FIG. 8.

Meanwhile, the distances between the first screw thread of the first portion are equal to the distances between the second screw thread of the second portion, and thus implantation torque is not sharply increased. Also, since the inner diameters of the second screw thread are less than the inner diameters of the first screw thread, a pressure is applied to a peripheral bone tissue and thus an initial fixing force may be increased.

As described above, according to the implant fixture 1 of the present embodiment, the initial fixing force may be sufficiently increased without a sharp increase of the implantation torque, and thus the implant fixture 1 may be stably and firmly implanted without damaging the peripheral bone structure.

Meanwhile, according to the present embodiment, the first and second screw threads have more than two threads to reduce an implanting time period. Also, as obvious via the result of FIG. 7, the present embodiment having two threads has a low maximum equivalent stress, and thus has a great stress dispersion effect.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. An implant fixture that is adapted to be implanted into a bone tissue including cortical bone and cancellous bone while rotating on a central axis to thereby form an artificial tooth root, the implant fixture comprising:
   a first portion that comprises a first screw thread having first peaks and first roots alternating with one another on an outer surface of the first portion; and
   a second portion that is disposed below the first portion, wherein a second screw thread having second peaks and second roots alternating with one another is formed on an outer surface of the second portion, wherein distances between adjacent second peaks of the second screw thread are equal to distances between adjacent first peaks of the first screw thread, and wherein outer diameters of the second screw thread are the same in up and down directions and inner diameters of the second screw thread are less than inner diameters of the first screw thread and inner diameters of the second screw thread are the same in up and down directions over the substantially whole length of the second portion; and
   a third portion that is disposed below the second portion, wherein a third screw thread having third peaks and third roots alternating with one another on an outer surface of the third portion, and
   wherein a cutting edge is caved to be more adjacent to the central axis than the third roots and is arranged only in the third portion and is arranged around the outer surface of the third portion below the screw thread,
   wherein the first screw thread and the second screw thread each have at least double threads, and
   wherein the outer diameter of the first screw thread and the outer diameters of the second screw thread are the same, and
   wherein the first screw thread and the second screw thread are continuously connected to each other wherein the third portion tapers such that outer diameters of the third screw thread decrease from an upper part of the third portion where the third screw thread abuts the second screw thread to a lower part of the third portion at an end of the implant fixture.

2. The implant fixture of claim 1, wherein all of the first peaks of the first screw thread and the second peaks of the second screw thread lie on a same plane.

3. The implant fixture of claim 1, wherein the inner diameters of the second screw thread are less than the inner diameters of the first screw thread by 0.1 to 1.0 mm.

4. The implant fixture of claim 1, wherein, when the distances between adjacent first peaks of the first screw thread are referred to as S1 and the distances between adjacent second peaks of the second screw thread are referred to as S2, S1 and S2 are between 0.6 to 1.0 mm.

5. The implant fixture of claim 1, wherein distances that the first screw thread and the second screw thread move per one rotation along a central axis are the same, and the distances are between 0.5 to 2.5 mm.

6. The implant fixture of claim 1, wherein the third portion tapers such that inner diameters of the third screw thread decrease from an uppermost part of the third portion where the third screw thread abuts the second screw thread to a lower part of the third portion at an end of the implant fixture.

* * * * *